United States Patent [19]

Cheng et al.

[11] Patent Number: 5,223,631

[45] Date of Patent: Jun. 29, 1993

[54] BIMETALLIC COMPLEXES AS CATALYSTS IN AN OXIDATION PROCESS

[75] Inventors: Cheu P. Cheng; Yaw H. Hwang; Ching C. Liu, all of Hsin, Taiwan

[73] Assignee: National Science Council, Taipei, Taiwan

[21] Appl. No.: 906,576

[22] Filed: Jun. 30, 1992

[51] Int. Cl.$^5$ ............... C07D 301/06; C07D 303/04; C07D 303/06

[52] U.S. Cl. ....................... 549/535; 556/1; 556/28; 556/45; 556/137; 556/150

[58] Field of Search ......................... 549/533

[56] References Cited

U.S. PATENT DOCUMENTS

| | | | |
|---|---|---|---|
| 3,007,944 | 11/1961 | Amir | 549/533 |
| 3,316,279 | 4/1967 | Fenton | 549/533 |
| 3,333,010 | 7/1967 | Urbanek | 549/533 |
| 3,472,876 | 10/1969 | Klein | 549/533 |
| 3,843,691 | 10/1974 | Bouboulis | 549/533 |
| 3,935,272 | 1/1976 | Chapurdit | 549/533 |
| 4,256,649 | 3/1981 | Dyer | 549/533 |
| 4,822,899 | 4/1989 | Groves et al. | 549/533 |

*Primary Examiner*—Joseph E. Evans
*Attorney, Agent, or Firm*—Morgan & Finnegan

[57] ABSTRACT

Disclosed is an olefin epoxidation process that contacting an olefinically unsaturated substrate with oxygen in the presence of catalytic amount of a bimetallic complex under the reaction conditions such that the olefin is at least partially oxidized. The metals introduced in the bimetallic complex are independently selected from vanadium, chromium, manganese, iron, cobalt, nickel, copper, molybdenum, ruthenium, rhodium, palladium, tungsten, rhenium, osmium, iridum or platinum.

9 Claims, No Drawings

BIMETALLIC COMPLEXES AS CATALYSTS IN AN OXIDATION PROCESS

BACKGROUND OF THE INVENTION

The present invention relates to a bimetallic complex which can be used as catalysts for the oxidation of hydrocarbons.

Epoxides are a general class of compounds which contain an oxirane ring. They are conventionally produced by oxidation of olefins. For example, ethylene oxide is produced by aerobic oxidation of ethylene in the presence of supported silver catalyst. However, this aerobic oxidation can not be used to produce propylene oxide from propylene efficiently. Propylene oxide is conveniently prepared by oxidation of propylene using peroxides in the presence of high valent metal oxide catalyst (J. Kollar, U.S. Pat. No. 3,351,635). Another method of preparing oxirane compound is through epichlorohydrin intermediate. U.S. Pat. No. 4,356,311 discloses the epoxidation of olefins using a transition metal nitrocomplex catalyst and a thallium(III) compound cocatalyst. A recent U.S. Pat. No. 4,822,899 discloses an olefin epoxidation process using metalloporphyrin complexes as catalyst and oxygen as oxidant in the substantial absence of cocatalyst or coreductant.

SUMMARY OF THE INVENTION

The present invention involves an oxidation process, especially an olefin epoxidation, that contacting an olefinically unsaturated substrate with oxygen in the presence of catalytic amount of a bimetallic complex under the reaction conditions such that the hydrocarbon is at least partially oxidized.

The special feature of the present invention is the use of bimetallic complexes as catalysts. Moreover, no other oxidant, such as peroxide, peracid or PhIO, cocatalyst, such as thallium(III), or coreductant are required to effect the present process. In addition, the present process can be effect at convenient temperature range.

DETAILED DESCRIPTION OF THE INVENTION

The present invention is a process of epoxidation reaction. It requires three essential ingredients, i.e., an olefin, an oxidizing agent and a catalyst. Solvent can be optionally employed in the epoxidation reaction. The solvent serves the purpose of dissolving the olefin and the catalyst. It can be chosen from a wide variety of compounds which allow the epoxidation reaction to proceed. Mixed solvent can also be employed as long as epoxidation reaction is allowed. Examples of solvents are N,N-dimethylformamide (DMF), N,N-dimethylacetamide, sulfolane, acetonitrile, chloroform, various ethers, propylene carbonate, benzene and its derivatives. Solvent containing suitable amount of dissolved solute can also be employed. Examples of solute are imidazole, pyrole, pyrolidine, oxazole, piperidine, pyridine, pyrimidine, pyrazine, histidine, trialkylamine, dialkylamine, alkylamine, alkylarylamine, and their derivatives. The concentration of the solute is in the range of 0.0 to 10.0 mole/liter. The amount of solvent employed can vary over a wide range. Typically from 0.0 to 1000 liter per mole of olefin.

The olefins can be aliphatic, aromatic, mixed aliphatic-aromatic, straight-, branched-chain, cyclic and combination thereof. The olefins can also contain substituent moieties which do not prevent epoxidation reaction, and which may contain elements other than carbon and hydrogen. Mixture of olefins can also be employed. Examples of olefins include propylene, butylene, cyclohexene, cyclooctene, trans-$\beta$-methylstyrene, trans-$\beta$-nitrostyrene, stilbene, unsaturated fatty acid, trans-methyl cinnamate, maleic anhydride, and allyl halide. More examples are mentioned in U.S. Pat. No. 4,356,311, the relevant teaching of which is incorporated herein by reference.

The oxidizing agent can be anything which is a source of oxygen under reaction condition. Oxygen can be supplied as pure oxygen, as air, or as air enriched with oxygen. The gaseous oxygen sources can also include diluent, such as $CO_2$, $N_2$, noble gas and steam. The oxygen partial pressure in the reaction vessel can range from 0.01 torr to 500 atm.

The catalyst of the present invention is a bimetallic complex of the formula:

wherein metals Ma and Mb can independently be vanadium, chromium, manganese, iron, cobalt, nickel, copper, molybdenum, ruthenium, rhodium, palladium, tungsten, rhenium, osmium, iridum and platinum. L is a multidentate ligand. It provides coordination sites to bind the two metals Ma and Mb. L has the general formula:

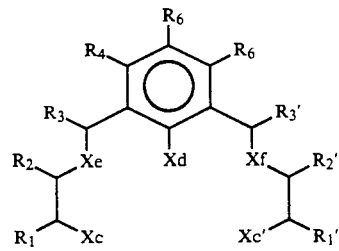

wherein Xc and Xc' can independently be O, S, amino or phosphino groups; Xd can be O, S; Xe and Xf can be independently N, P, O and S; $R_1$, $R_2$, $R_3$, $R_1'$, $R_2'$, and $R_3'$ can independently be hydrogen, halo, nitro, cyano, amino, hydroxyl, alkoxyl, acyl, carboxylate, alkyl, substituted alkyl group, aryl, substituted aryl group, carbonyl, and imino groups. It should be pointed out that C—$R_1$ and C—$R_2$ or C—$R_1'$ and C—$R_2'$ may independently form a cyclic group such as cyclohexyl group or phenyl group with suitable substituents. For example, when C—$R_1$ and C—$R_2$ form a phenyl group, it has the general structure:

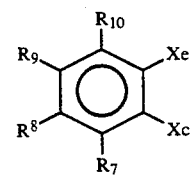

wherein the substituents $R_7$, $R_8$, $R_9$ and $R_{10}$ may independently be hydrogen, halo, nitro, cyano, amino, hydroxyl, alkoxyl, acyl, carboxylate, alkyl, substituted alkyl group, aryl, substituted aryl group. C—$R_2$ and C—$R_3$, or C—$R_2'$ and C—$R_3'$ can also independently form a cyclic moieties, together with Xe, they can form pyrolyl, imidazolyl, pyrolidyl, piperidyl, pyridyl, pyrimidyl, pyrazyl, oxazolyl, pirazyl or the above group with substituents. For example, C—$R_2$—Xe—C—$R_3$ can form a substituted pyridyl group of the general formula:

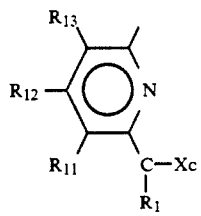

wherein $R_{11}$, $R_{12}$ and $R_{13}$ can independently be hydrogen, halo, nitro, cyano, amino, hydroxyl, alkoxyl, acyl, carboxylate, alkyl, substituted alkyl group, aryl, substituted aryl group. $R_4$, $R_5$, and $R_6$ can independently be hydrogen, halo, nitro, cyano, amino, hydroxyl, alkoxyl, acyl, carboxylate, alkyl, substituted alkyl group, aryl, and substituted aryl group. La and Lb are acceptable ligands coordinated to Ma and Mb, respectively. n1 and n2 are integers between 0 and 3 inclusive. For example, La and Lb can be pyridine or acetonitrile and na=nb=1. Xa is an acceptable ligand bridging the two metal ions. Examples of bridging ligand are hydroxylate, alkoxylate, pyrazolate, carboxylate, azide, and halides. n3 can range between 0 and 3 inclusive. Xb is counter ion which provide the required charge balance. Examples of Xb are halides, perchlorate, acetate, borontetrafluoride, phosphorushexafluoride, nitrate, thiocyanate. In fact most of anions and cations can be employed to balance the charge on the metal containing moiety. n4 can range from 0 to 4 inclusive.

Specifically, preferred bimetallic complexes of the present invention have the general formula of:

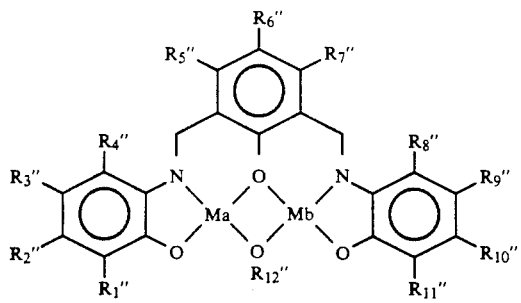

wherein $R_1''$ to $R_{11}''$ are independently selected from hydrogen, halo, nitro, cyano, amino, hydroxyl, alkoxyl, acyl, carboxylate, alkyl, substituted alkyl group, aryl, and substituted aryl group. And $R_{12}''$ can be hydrogen, alkyl group which may contain atoms other than hydrogen and carbon.

The catalyst is employed in a catalytic amount. It can be employed in the concentration range from $10^{-5}$ M/l to 2.0 M/l. The actual concentration depends on the nature of the catalyst, olefin, and solvent used. The preferred catalyst concentration is from $10^{-4}$M to 1M. The catalyst can also be employed on a solid support. Under this situation, the catalyst concentration is such that the catalyst occupies from 0.01% to 100% of the available support surface sites.

The process of the present invention can be conducted under any combination of temperatures and pressures at which the reaction proceeds. Typically the reaction is conducted from 0° C. to 800° C., and preferably from 0° C. to 500° C. The epoxidation reaction can be conducted at pressure from 10 torr to 500 atm.

The following examples are given to illustrate the present invention and should not be construed as limiting its scope.

Example 1: Preparation of 2,6-bis[(2-oxophenyl)iminomethyl]-4-methylphenolato-$\mu$-hydroxodicobalt(II), $Co_2(\mu\text{-OH})L$, complex 1

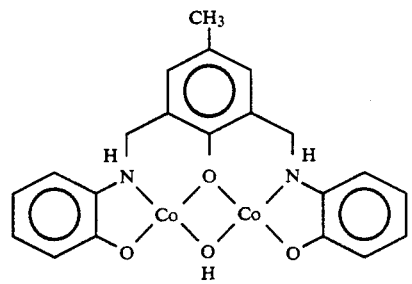

Complex 1 is prepared by adding aqueous solution of $Co(NO_3)_2 \cdot 6H_2O$ (0.61 g in 50 ml water) dropwisely to a stirred methanol solution containing 0.34 g $H_3L$ and 0.12 g NaOH. The solution is heated to reflux for 4 hrs with constant stirring. The solid product, obtained after filtering the reaction mixture, can be purified by recrystallization using dichloromethane as solvent. The ligand $H_3L$, 2,6-bis[(2-hydroxyphenyl)iminomethyl]-4-methylphenol, is prepared by the reaction between 2,6-diformyl-4-methylphenol and 2-hydroxyaniline with reference to the literature method in Inorg. Nucl. Chem. Lett. 1970, 6, 125 by R. Robson. 2,6-diformyl-4-methylphenol is also prepared by the literature method described in Chem. Ber. 1909, 42, 2534 by G. Ullman and K. Brittner.

Example 2: Preparation of 2,6-bis[(2-oxophenyl)iminomethyl]-4-methylphenolato-$\mu$-methoxodicobalt(II), $Co_2(\mu\text{-OMe})L$, complex 2

A 120 ml methanol solution containing complex 1 (0.5 g) and $NaOCH_3$ (0.07 g) was heated to reflux for 3 hours. Then, the solution was reduced to 30 ml in a rotary evaporator and stored in a refrigerator to allow precipitation. The product was collected by filtration.

Example 3: Preparation of 2,6-bis[(2-oxophenyl)aminomethyl]-4-methyolphenolato-$\mu$-hydroxodicobalt(II), $Co_2(\mu\text{-OH})L'$, complex 3

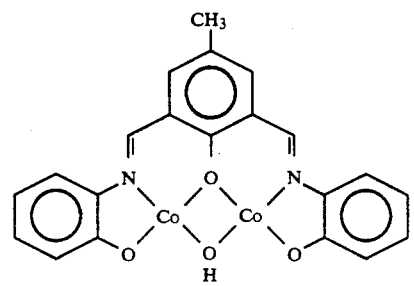

$H_3L'$ is prepared by reduction of $H_3L$ with $NaBH_4$. The details are described below. A 40 ml THF solution containing 0.346 g $H_3L$ and 0.378 g of $NaBH_4$ is heated to reflux for 6 hrs. After filtering, the filtrate is neutralized with 2M HCl methanol solution. Filter again, evaporate the solvent in the filtrate to obtain H$_3$L'.

The preparation of Co$_2$($\mu$-OH)L', complex 3, is essentially the same as the preparation of complex 1, except that H$_3$L' is used in place of H$_3$L in example 1.

Example 4: Preparation of 2,6-bis[(2-oxophenyl)iminomethyl]-4-methylphenolato-$\mu$-hydroxodiiron(II), Fe$_2$($\mu$-OH)L, complex 4

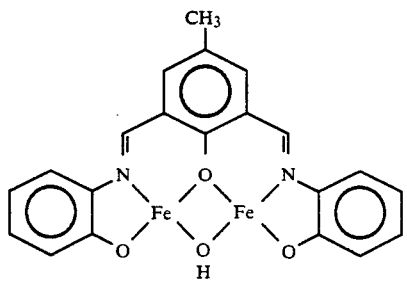

Complex 4 is prepared by adding FeCl$_2$ methanol solution (0.4 g FeCl$_2$·4H$_2$O in 100 ml methanol) dropwisely into refluxing 100 ml methanol solution containing 0.346 g H$_3$L and 0.16 g NaOH. After completion, the solution is further heated for 15 min. The solid precipitate is collected by filtration. After drying, extract with dichloromethane. Complex 4 is obtained by evaporating dichloromethane. All operations are carried out in the absence of oxygen.

Example 5: Preparation of 2,6-bis-[(2-oxo-5-tert-butylphenyl)iminomethyl]-4-tert-butylphenolato-$\mu$-hydroxodiiron(II), Fe$_2$($\mu$-OH)L'', complex 5.

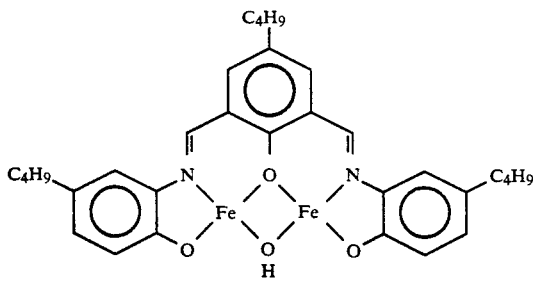

The ligand H$_3$L'' is prepared by reacting 2.06 g 2,6-diformyl-4-tert-butylphenol with 2.5 g 2-amino-4-tert-butylphenol in methanol solution for 3 hrs under refluxing condition. Evaporate the solvent, and recrystallize with dichloromethane/hexane (1:1) mixed solvent. Complex 5 is prepared by adding methanol solution of FeCl$_2$ (0.4 g FeCl$_2$·4H$_2$O in 100 ml methanol) dropwisely into a refluxing methanol solution containing 0.5 g H$_3$L'' and 0.16 g NaOH. After completion, the solution is further heated for 15 min. Filter and keep the filtrate. After the volume of filtrate is reduced to about 10 ml, then 10 ml of water is added. Dry the precipitate and recrystallize in dichloromethane/hexane (1:1) solution. All operations are carried out in the absence of oxygen.

Example 6: Preparation of 2,6-bis[(2-oxophenyl)iminomethyl]-4-methylphenolato-$\mu$-hydroxocopper(II)iron(II), CuFe($\mu$-OH)L, complex 6.

A methanol solution (5 ml) containing 0.482 g Cu(NO$_3$)$_2$·3H$_2$O was added to a 20 ml tetrahydrofuran solution containing 0.692 g H$_3$L. After the mixture was refluxed for 30 min, the solid precipitate was collected by filtration. This solid was redissolved in 100 ml dimethylformamide (DMF). An aqueous solution (5 ml) containing 0.04 g sodium hydroxide was added to this DMF solution. After refluxing for 30 min, an aqueous solution (40 ml) containing 0.11 g FeCl$_2$·4H$_2$O was slowly added to it. Refluxing for another 30 min, collect the filtrate after filtering. The solvent in the filtrate was then removed. The residue was extracted with dichloromethane. The catalyst, complex 6, which contained a copper and an iron was obtained after the dichloromethane was removed.

Examples 7-18

Catalyst, as prepared in Example 1-6, was dissolved in 10 ml DMF, unless otherwise specified, in a concentration range between 10$^{-4}$ and 10$^{-1}$M. A quantity of olefin was then added to the catalyst solution. The solution was then put in a closed glass vessel which was filled with the oxygen gas. The solution was then heated to 100° C. and the epoxidation reaction proceeds smoothly. After 24 hrs, the product was analyzed by TLC. Epoxide was the major product with high selectivity. And trans-olefin yielded trans-epoxide; cis-olefin yielded cis-epoxide. The results were summarized below.

TABLE 1

| No[a] | Cat[b] | C1[c] (10$^{-3}$ M) | PO$_2$ Atm | Olefins | C2[d] M | Y[e] |
|---|---|---|---|---|---|---|
| 7 | 1 | 20 | 0.91 | E-stilbene | 0.335 | 10.0 |
| 8 | 1 | 10 | 0.91 | Z-stilbene | 0.335 | 12.0 |
| 9 | 1 | 10 | 0.91 | trans-$\beta$-nitrosytrene | 0.335 | 30.0 |
| 10 | 1 | 10 | 0.91 | trans-$\beta$-methylstyrene | 0.335 | 1.7 |
| 11 | 1 | 10 | 0.91 | cyclooctene | 0.335 | 0.6 |
| 12[f] | 1 | 10 | 0.91 | E-stilbene | 0.335 | 5 |
| 13[g] | 1 | 10 | 0.91 | E-stilbene | 0.335 | 16 |
| 14 | 2 | 10 | 0.91 | E-stilbene | 0.335 | 11 |
| 15 | 3 | 10 | 0.91 | E-stilbene | 0.335 | 12 |
| 16 | 4 | 1.2 | 0.95 | cyclooctene | 0.278 | 67.3 |
| 17[h] | 5 | 0.22 | 0.95 | cyclooctene | 0.182 | 400 |
| 18 | 6 | 20 | 0.91 | E-stilbene | 0.5 | 5 |

[a]Example Number;
[b]Designate the complex prepared in Examples 1-6;
[c]Concentration of catalyst;
[d]Concentration of olefin;
[e]The number of moles of epoxide formed per mole of catalyst after 24 hrs reaction time;
[f,g] and [h]Note for reaction employing solvent other than DMF, where[f]Sulfolane was used as solvent, [g]Sulfolane with 0.5% pyridine was used as solvent, and [h]Reaction conditions are: in pure cyclooctene, at temperature 393K.

Although the present invention has been described in some detail by illustrations and examples, for manifestation, certain changes and modifications may be introduced within the scope of the appended claims.

What is claimed is:

1. An epoxidation process of olefins comprising contacting the olefins with an oxidizing agent in the presence of a catalytic amount of a bimetallic complex, wherein the bimetallic complex has the general formula of:

M$_a$M$_b$L(La)$_{n1}$(Lb)$_{n2}$(Xa)$_{n3}$(Xb)$_{n4}$ wherein Ma and Mb are independently selected from the group consisting of vanadium, chromium, manganese, iron, cobalt, nickel, copper, molybdenum, ruthenium, rhodium, palladium, tungsten, rhenium, osmium, iridum and platinum;

L has the general structure of:

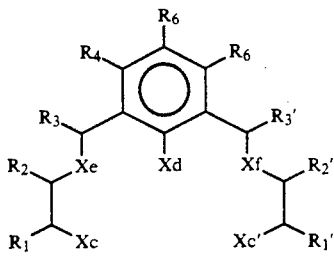

wherein Xc and Xc' are independently selected from the group consisting of O, S, amino, and phosphino groups;

Xd is selected from the group consisting of O and S;

Xe and Xf are independently selected from the group consisting of N, P, O, and S;

$R_1$, $R_2$, $R_3$, $R_1'$, $R_2'$ and $R_3'$ are independently selected from the group consisting of hydrogen, halo, nitro, cyano, amino, hydroxyl, alkoxyl, acyl, carboxylate, alkyl, substituted alkyl group, aryl, substituted aryl group, carbonyl, and imino groups;

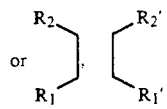

independently form a cyclic moieties;

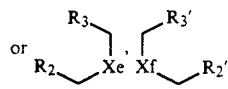

independently form a heterocyclic moieties with the nitrogen atom selected from the group consisting of pyrolyl, imidazolyl, pyrolidyl, piperidyl, pyridyl, pyrimidyl, pyrazyl, oxazolyl, pirazyl, and the above-mentioned group with substituent; and $R_4$, $R_5$, and $R_6$ are independently selected from the group consisting of hydrogen, halo, nitro, cyano, amino, hydroxyl, alkoxyl, acyl, carboxylate, alkyl, substituted alkyl group, aryl, and substituted aryl group; and La and Lb are acceptable ligands coordinated to Ma and Mb respectively;

Xa is an acceptable ligand bridging Ma and Mb;

Xb is a counter ion which provides the required charge balance;

n1 and n2 are integers between 0 and 3 inclusive;

n3 is an integer between 0 to 3 inclusive; and n4 is an integer between 0 to 4 inclusive.

2. An epoxidation process as claimed in claim 1, wherein the olefins is selected from the group consisting of alkene with 2-30 carbon atoms, and alkene which contains elements other than carbon and hydrogen.

3. An epoxidation process as claimed in claim 2, wherein the olefin is selected from the group consisting of ethylene, propylene, butylene, cyclohexene, unsaturated fatty acid, trans-methylcinamate, maleic acid, and allyl halide.

4. An epoxidation process as claimed in claim 1, wherein the oxidizing agent is oxygen gas.

5. An epoxidation process as claimed in claim 1, wherein Ma and Mb are independently selected from the group consisting of cobalt, copper and iron.

6. An epoxidation process as claimed in claim 1, wherein

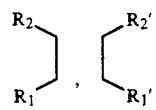

independently form a cyclic moieties selected from the group consisting of cyclohexyl group and phenyl group with substituents.

7. An epoxidation process as claimed in claim 1, wherein La and Lb are selected from the group consisting of pyridine, imidazole and derivatives thereof.

8. An epoxidation process as claimed in claim 1, wherein Xa is selected from the group consisting of hydroxylate, alkoxylate, pyrazolate, carboxylate, halides, and azide.

9. An epoxidation process as claimed in claim 1, wherein Xb is selected from the group consisting of halides, perchlorate, acetate, borontetrafluoride, phosphorus hexafluoride, nitrate and thiocyanate.

* * * * *